United States Patent [19]

Leifheit

[11] Patent Number: 4,998,671
[45] Date of Patent: Mar. 12, 1991

[54] MULTIPLE COMPARTMENT FLEXIBLE PACKAGE

[75] Inventor: David H. Leifheit, Cincinnati, Ohio

[73] Assignee: The Drackett Company, Cincinnati, Ohio

[21] Appl. No.: 424,851

[22] Filed: Oct. 20, 1989

[51] Int. Cl.[5] ............................................. A61L 9/04
[52] U.S. Cl. ...................................... 239/44; 239/51.5;
239/56; 222/94; 206/219
[58] Field of Search ....................... 239/34, 42, 43, 44,
239/51.5, 55, 56, 304, 309; 222/94, 145, 187;
206/219, 221

[56] References Cited

U.S. PATENT DOCUMENTS

| | | |
|---|---|---|
| 2,209,914 | 7/1940 | Gerber et al. . |
| 2,699,779 | 1/1955 | Lustig ................................ 222/187 |
| 2,714,382 | 8/1955 | Alcala . |
| 2,864,492 | 12/1958 | Lappala . |
| 2,940,449 | 6/1960 | Thomson . |
| 3,343,664 | 9/1967 | Poitras . |
| 3,367,785 | 2/1968 | Finucane et al. .................... 206/525 |
| 3,478,871 | 11/1969 | Sager ................................... 206/221 |
| 3,608,709 | 9/1971 | Pike . |
| 3,889,804 | 6/1975 | Ravich ................................ 206/221 |
| 4,145,001 | 3/1979 | Weyenberg et al. . |
| 4,161,283 | 7/1979 | Hyman . |
| 4,161,284 | 7/1979 | Rattan ................................. 239/56 |
| 4,277,024 | 7/1981 | Spector . |
| 4,345,716 | 8/1982 | Armstrong et al. . |
| 4,362,241 | 12/1982 | Williams ............................. 206/219 |
| 4,372,098 | 2/1983 | Mason . |
| 4,502,630 | 3/1985 | Haworth et al. . |
| 4,511,533 | 4/1985 | Guadagno et al. ................. 206/219 |
| 4,534,509 | 8/1985 | Holzner . |
| 4,558,820 | 12/1985 | Harris, Jr. . |
| 4,660,763 | 4/1987 | Gutkowski et al. . |
| 4,762,124 | 8/1988 | Kerch et al. . |

Primary Examiner—Andres Kashnikow
Assistant Examiner—Karen B. Merritt
Attorney, Agent, or Firm—Gene Warzecha

[57] ABSTRACT

A multiple compartment flexible package having a receiving compartment adapted to contain one or more liquid impermeable, rupturable containers, a dispensing compartment containing an absorbent material and a passageway interposed between the compartments. Upon the application of pressure to the receiving compartment, the inner liquid container is ruptured and the liquid bursting from the inner container is directed by the passageway to the absorbent material within the dispensing compartment. The liquid contents of the inner container are absorbed by the absorbent material and dispensed therefrom at a rate depending upon the application of the package. The dispensing compartment may have a portion thereof permeable to the liquid contents or may have one or more apertures in one surface thereof adjacent the absorbent material.

8 Claims, 3 Drawing Sheets

MULTIPLE COMPARTMENT FLEXIBLE PACKAGE

BACKGROUND OF THE INVENTION

1. Field of the Invention

The invention relates generally to applicators and dispensers for releasing predetermined quantities of liquid or vaporizable material. More particularly, the invention relates to flexible liquid containing packages comprising multiple compartments for maintaining at least one liquid composition isolated from the ambient until use.

2. Description of the Prior Art

Flexible packages for containing a variety of solid or liquid substances are commonly used in order to enable a user to conveniently handle the contained product until immediately prior to use at which time the package may be relatively easily opened. As used herein, the term "flexible" means a generally flat package or pouch formed from a pair of thin, pliable sheet members sealed together to form an interior space. Often the contents of the flexible package include at least one additional internal container (within the interior space) filled with a material which must be maintained separate from the remaining contents of the package until immediately prior to use.

For example, U.S. Pat. No. 2,864,492 (Lappala) shows a flexible package having an outer container containing a polymerizable material as well as a separate, inner rupturable container (pocket or capsule) containing a catalyst. The outer container is made of material impervious to liquids and impervious to the particular polymerizable material contained within. When the inner container is ruptured and the contents of the inner and outer containers are mixed, the outer container may be cut to release the mixed contents. Another example of a multiple compartment flexible package is shown in U.S. Pat. No. 3,343,664 (Poitras) which discloses a dispenser of a vaporizable liquid composition, the dispenser having a rupturable, liquid impermeable inner pouch within a permeable outer pouch, the inner pouch adapted to be torn without tearing the outer pouch.

Flat, multicompartment, flexible packages have been adapted for dispensers of air-treating products as disclosed in U.S. Pat. Nos. 4,558,820 (Harris Jr.) and 4,502,360 (Haworth et al). Each of these patents shows an air-treating, vapor dispensing device in the form of a flat permeable dispensing pouch supported between a pair of rigid, apertured support members, the pouch including an impermeable inner storage container filled with a flowable, vaporizable air-treating composition. The dispenser is activated when the inner container is ruptured by forcing the two opposing support members together to thereby release the composition into the flexible permeable dispensing pouch. The composition diffuses through the surfaces of the pouch and is released at the outer surfaces of the pouch as a vapor.

One disadvantage of all known flexible packages having sealed outer containers and rupturable inner containers is that they may rupture at the outer seal if the inner seal breaks at a point which directs the bursting force directly at the outer sealed edge. This is especially true if the outer edge is heat sealed. U.S. Pat. No. 4,660,763 (Gutkowski et al.) recognizes this disadvantage and discloses an air freshener having a reservoir for receiving the liquid in the pouch should the outer seal break upon activation. Nevertheless, in some instances leaks still occur.

Another disadvantage of prior art flexible pouches is that when they are supported vertically (as in Harris, Jr.) the liquid contents tend to pool in the bottom of the outer pouch, thus decreasing operational efficiency, unless the opposing surfaces of the package are kept very close together by an auxiliary support frame to keep the liquid spread out by adhesive attraction between the liquid and the surfaces. Harris, Jr. also provides an auxiliary support frame having a pair of opposed vertical planar supports which keep the pouch flat thereby relatively evenly distributing the liquid throughout the pouch.

It is an object of this invention to provide a dispenser of air-treating compositions in the form of a flat, flexible package which avoids pooling and achieves even distribution of liquid over a large portion of a flexible package without the necessity for auxiliary rigid support structures.

Some flexible packages such as those shown in U.S. Pat. Nos. 3,608,709 (Pike) and 4,534,509 (Holzner) use multiple compartments separated by an internal seal intended to rupture to enable communication between the compartments. The Holzner patent discloses a multiple compartment plastic package where the compartments are separated by a rupturable seal formed by the opposing sides of the plastic package being sealed along a rupturable, polymer plastic foam material. Holzner is directed in part to a mechanism to control rupture strength by inserting the polymeric material between the package sides which are sealed together. The manufacturing complexity of this structure is an obvious disadvantage.

The possibility of rupturing the outer package seal has received considerable attention in the prior art and numerous sealing techniques are known in addition to Holzner. Prior art dispensers have generally attempted to solve the bursting force problem by either providing excessive volume in the outer pouch (as shown, for example, in the Hayworth, Harris, Jr., and Gutkowski patents) or by providing separate compartments separated by a breakable seal (as shown in Pike and Holzner). In addition to integrity of the seal itself, volumetric capacity of multi-compartment flexible packages must be considered. Excessive volume in the outer pouch would cause it to act as a reservoir and allow liquid to pool. Too little volume in the outer pouch may, in addition to risking breaking the outer seal, prevent the liquid bursting from the inner pouch from flowing around the "squeeze point".

It is another object of this invention to provide a multiple compartment, flexible package having a rupture force control mechanism for reducing the force directed against the outer seal upon rupture of an inner, liquid bearing container. As will be shown below, the present invention effects rupture force control through an impregnatable member which acts somewhat as a shock absorber and provides additional advantages.

An additional advantage provided by the present invention is the combination of the composition-segregating characteristics of multiple compartment packages with liquid applicators. Thus, liquid-impregnated cleaning absorbent members or wipes may be maintained dry prior to use. It is known to provide packages, in both air diffusion and liquid applicator embodiments, having already impregnated absorbent member sealed by impenetrable barrier films. For example, U.S. Pat. No. 4,277,024 (Spector) discloses an aroma-dispensing tab in a package which is stickable onto a surface. The tab comprises an impregnated base with a perforated dome and is hermetically sealed in a foil package which must be torn open to remove the tab. U.S. Pat. No. 4,762,124 (Kerch et al.) and U.S. Pat. No. 4,372,098 (Mason) each disclose an impregnated, absorbent applicator for dispensing liquid. In Kerch the applicator is supported on a support layer and covered by a permeable dispensing membrane which is in turn covered by an impervious cover which must be peeled away prior to use. All the various layers are sealed together along a common boundary. The Mason structure is similar but without the intermediate permeable membrane. U.S. Pat. No. 4,145,001 (Weyenberg et al.) and U.S. Pat. No. 4,161,283 (Hyman) disclose a similar structure for dispensing volatile substances through a permeable membrane (rather than liquid per se). The devices of these patents necessarily use a relatively large amount of barrier film because the already impregnated absorbent member must be completely covered. The volume and surface area of the absorbent member must necessarily be greater than that of any container of the active material alone. Consequently, the amount of barrier material required is significantly greater than if the active liquid had been maintained in a separate compartment (as in the air diffusion devices) which could be subsequently ruptured immediately prior to use.

It is another object of this invention to provide a liquid applicator or dispenser in which the liquid is maintained separate from an impregnatable or absorbment member until just prior to use, thereby decreasing the amount of liquid-impervious barrier material required to preserve the liquid.

Very often the difference between vapor dispensing packages and liquid applicator packages is one of degree. For example, in those prior art embodiments of flexible packages containing absorbent material, the absorbent material is permitted to retain only a relatively small amount of active vaporizable material so that an accumulation of liquid is prevented since the object of the device in these cases is to dispense vapor, not liquid. In those embodiments where the device is intended to be used as a liquid applicator, the absorbent material is provided with a sufficient amount of liquid to enable the liquid to be dispensed. In both instances, the package must be sealed prior to use. In any event, prior art liquid applicators are generally not adaptable for use as air diffusers and vice versa. It would improve manufacturing efficiencies to produce a flexible package capable of easily being adapted to either use. It would further be desirable to provide a liquid applicator package incorporating some of the technology associated with air treating dispensers (such as keeping active components separated until immediately prior to use). Having a package adaptable to either use would be a benefit because a common, base package easily adaptable for one use or the other with a minimal number of manufacturing changes.

It is a further object of this invention to provide a dispenser suitable, with only minor changes, for either the application of liquids to a desired surface or the dispensing of vaporizable air-treating compositions.

No one prior art multiple compartment flexible package is able to efficiently mix a plurality of separated compositions without repeatedly transfering them between the original compartments (as in Holzner) or kneading the package (as in Lappala and Poitras). It is, therefore, a further object of this invention to provide a multiple compartment flexible package capable of efficiently mixing liquid components without additional manipulation.

It is yet another object of this invention to provide a multiple compartment flexible package enabling the impregnation of an absorbent dispensing member prior to use rather than at the time of manufacturing.

SUMMARY OF THE INVENTION

These and other objects of this invention are achieved by the preferred embodiment thereof in the form of a multiple compartment package comprising: a receiving compartment formed from a pair of peripherally sealed, pliable first sheet members; at least one liquid bearing inner container within said receiving compartment, said inner container adapted to be rupturable upon the application of pressure to release the contents of said inner container into said receiving compartment; a dispensing compartment for receiving the liquid contents of said inner container from said receiving compartment, said dispensing compartment formed from a pair of peripherally sealed, pliable second sheet members, at least a portion of said dispensing compartment provided with an area through which said liquid contents could be dispensed; an absorbent member within said dispensing compartment for absorbing said contents; and passageway means interposed between said receiving compartment and said dispensing compartment for directing said contents onto said absorbent member.

DESCRIPTION OF THE PREFERRED EMBODIMENT

Figure 2:
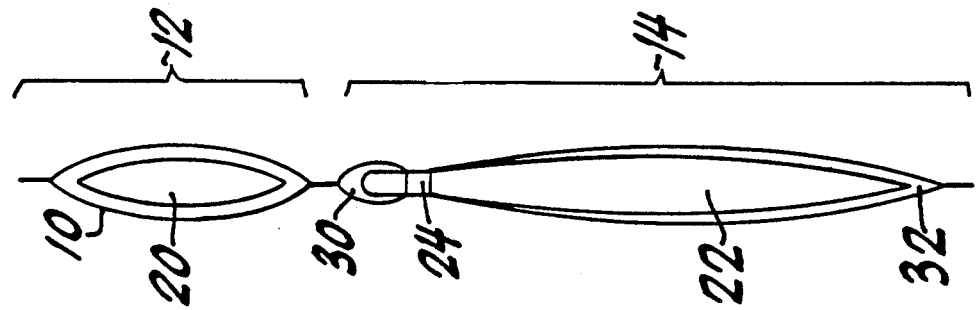
FIG. 2 is a schematic side elevational view of FIG. 1.
Figure 1:
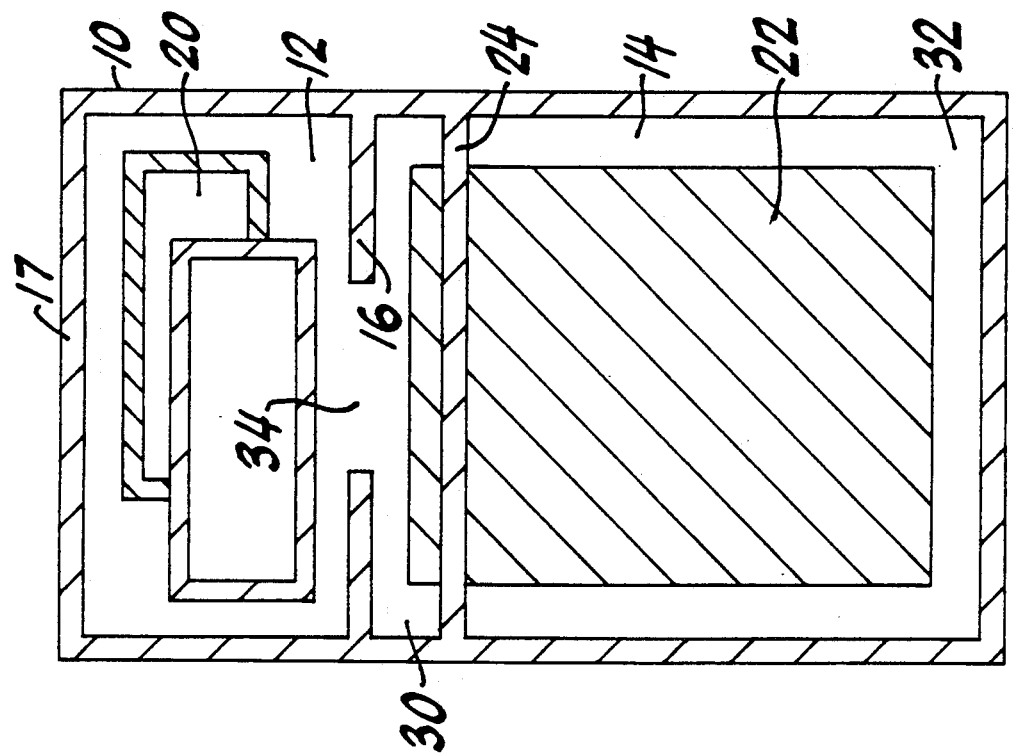
FIG. 1 is a schematic front elevational view of multiple-compartment flexible package constructed in accordance with the principles of this invention.

Referring now to FIGS. 1 and 2, a preferred embodiment of the invention is shown as a multiple compartment flexible package or container 10 comprising an upper receiving compartment 12 and a lower dispensing compartment 14 separated by a partial transverse seal 16. Container 10 is a generally planar structure formed from a pair of pliable sheet members peripherally sealed at perimeter 17 in a conventional manner. In the preferred embodiment, the material of the sheet members may be any one of a number of thermoplastic materials in order to enable portions of the opposing sheet members to be heat-sealed together to define the various parts of the package. Except as otherwise noted below, the material is also substantially impermeable to the package contents.

Receiving compartment 12 contains one or more rupturable inner containers or pouches 20 freely movable within the receiving compartment. Each pouch 20 is impermeable to its contents and may, depending upon the desired use for container 10, contain a component of a liquid cleaning, air-freshening and/or malodor-counteractant composition, etc. If package 10 is intended to be an air-treating product such as a deodorizer, the two inner pouches may be provided to separately contain, for example, solutions of sodium chlorite and citric acid. These solutions must be kept separate until use at which time they may be mixed to produce chlorine dioxide, a gas which would diffuse through the apertures of package 10 to neutralize odors such as tobacco smoke. If package 10 is intended to be used as a cleaning wipe, one inner pouch containing, for example, Stoddards solvent would be sufficient to enable package 10 to be used as a fabric spot remover as will be better understood below.

Dispensing compartment 14 contains an absorbent member 22 retained within the compartment by a transverse heat seal 24. The latter essentially divides dispensing compartment 14 into an upper, product-receiving portion 30 and a lower, product-dispensing portion 32. Member 22 may be any suitable absorbent material. For example, in the preferred embodiment, the absorbent material is a non-woven fabric or paper which is heat-sealable to the material of the pouch but not heat-sealable within itself. Member 22 need not be secured to the facing internal surfaces of the pouch. What is required is that the liquid contents of pouch or pouches 20 be constrained to flow through member 22. Heat seal 24 is merely one way of directing fluid flow through member 22. A possible alternative fluid flow constraint could be produced by making member 22 oversized to completely fill dispensing compartment 14. Because of the constraints on fluid flow, the liquid absorbed by member 22 passes from product-receiving portion 30, past heat seal 24 to product-dispensing portion 32 and throughout member 22. As stated, transverse heat seal 24 is one example of a means to ensure optimized absorption. That is, the package contents are prevented by the heat seal from flowing around member 22 and are directed entirely through it. If member 22 is too large, it may be folded to fit into dispensing compartment 14. Alternatively, a non-folded form of absorbent material may be used provided it has sufficient thickness and density to obviate folding (e.g. felt, "blotter" paper, etc.).

Seal 16 is provided with a restricted central opening or passageway 34 which serves to direct the liquids bursting from flexible pouch or pouches 20 onto that portion of absorbent member 22 adjacent restricted opening 34. While seal 16 is shown to be straight, any other shape may be utilized provided the remaining features of the invention are incorporated. Because of the wick nature of member 22 and the central positioning of opening 34, the absorbed liquid is quickly and evenly distributed throughout member 22. The thickness and density of absorbent member 22 is selected to be that which is necessary to absorb the volume of liquid contained within pouches 20 and to produce a usable degree of saturation of the member in product-dispensing portion 30. The absorbent member of the preferred embodiment overcomes the liquid pooling problems associated with prior art devices such as that described in the aforementioned patent to Harris Jr. The wicking action of the absorbent member retains the liquid evenly distributed all over itself without the necessity for any externally imposed force from auxiliary support members as in the aforementioned Harris Jr. device.

The degree of restriction in opening 34 depends upon the volume and number of inner pouches 20. If a plurality of inner pouches 20 are used, then restricted opening 34 should be less than half the total width of heat seal 16 and preferably close to one third. The restriction enhances the ability of the opening to mix a plurality of liquids by directing them through a confined space and onto the portion of member 22 exposed between transverse seal 24 and restricted opening 34. Mixing is then completed as the plurality of liquids wick together throughout the rest of member 22.

The outer pouch should be made from a pliable polymeric film having an intrinsic permeability less than that value at which the liquid cleaning, air freshening, and/or malodor counteractant compositions of interest could penetrate the film to the extent of wetting the outer surface, forming droplets or leaking out under their own weight. Furthermore, the permeability within this limit should be primarily due to diffusion through the film and absorption should be only a relatively small contribution.

The preferred embodiment minimizes the risk of having the bursting force of the inner pouch possibly breach the outer seal by providing the absorbent member which acts as a shock absorber as well as a liquid absorber. This enables the inner pouch to be constructed without precise manufacturing controls directed to reducing the bursting force.

It has been found that the volume of receiving compartment 12 should be no less than about $1\frac{1}{2}$ times the volume of the inner storage pouch or pouches 20 and no greater than about 4 times the volume of the inner pouches. When the receiving compartment is squeezed to burst the inner pouches, the receiving volume should be enough to allow the burst liquids to flow around the squeeze point and through restricted opening 34. Excessive volume in the receiving compartment 12 would make it act as a reservoir to hold the liquid rather than direct it to the dispensing compartment 14.

Figure 4:
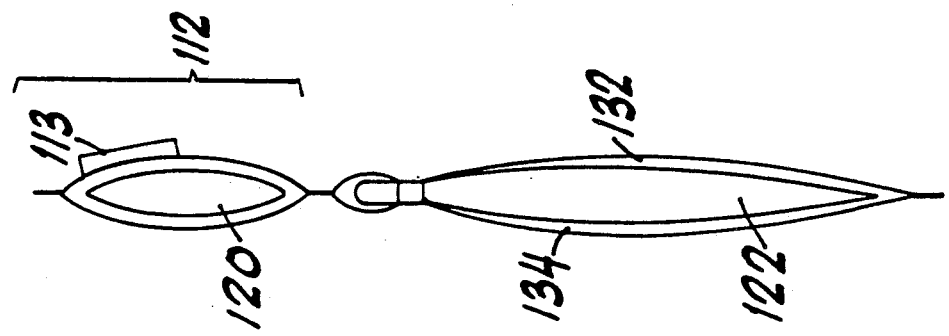
FIG. 4 is a schematic, side elevational view of FIG. 3.
Figure 3:
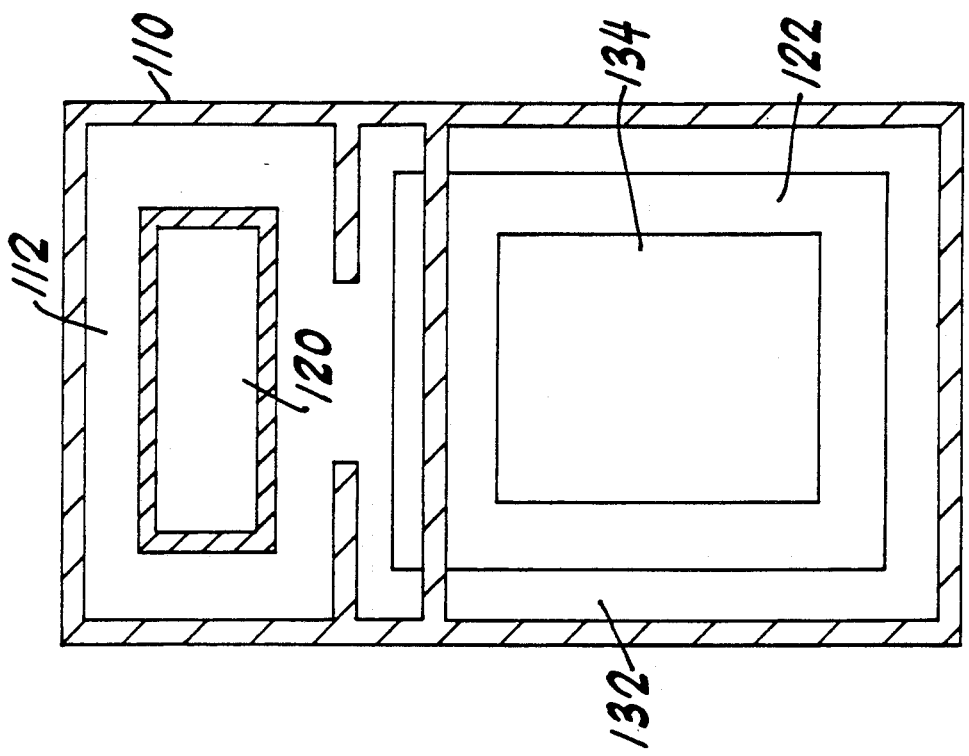
FIG. 3 is a schematic front elevational view of an alternate embodiment of the invention.

In the embodiment shown in FIGS. 1 and 2, the package 10 is used as, for example, an air freshener with product-dispensing portion 32 made permeable to the liquid absorbed by member 22. The active ingredient absorbed by member 22 diffuses slowly through the permeable surfaces of product-dispensing portion 32 in a conventional manner. Alternatively, a package 110 could be configured with a product-dispensing portion 132 provided with a single large aperture 134 exposing member 122, as shown in FIG. 3. Member 122 may, but need not be, secured to the inner peripheral surface of aperture 134. Leakage will not occur through the space between member 122 and the peripheral edge of aperture 134 because the liquids are constrained to flow through and be absorbed totally by member 122. As shown in FIG. 4, package 110 lends itself to a convenient, cleaning wipe embodiment. Receiving compartment 112 is provided with one or more adhesive members or tapes 113 enabling it to be secured in a desired position. For example, receiving compartment 112 could be folded over to cover the absorbent member 122 exposed through opening 134 and secured in that position by sticking adhesive tapes 113 to a portion of the bottom end of package 110. The package is sufficiently pliable and sufficiently long to enable tapes 113 to be properly positioned. When the package is to be used, it would be unfolded, inner pouch 120 would be broken and the contents absorbed by member 122. The receiving compartment 112 could be folded back and tapes 113 would be attached to the back of the product dispensing portion 132, thus producing a loop for the user's fingers.

Figure 5:
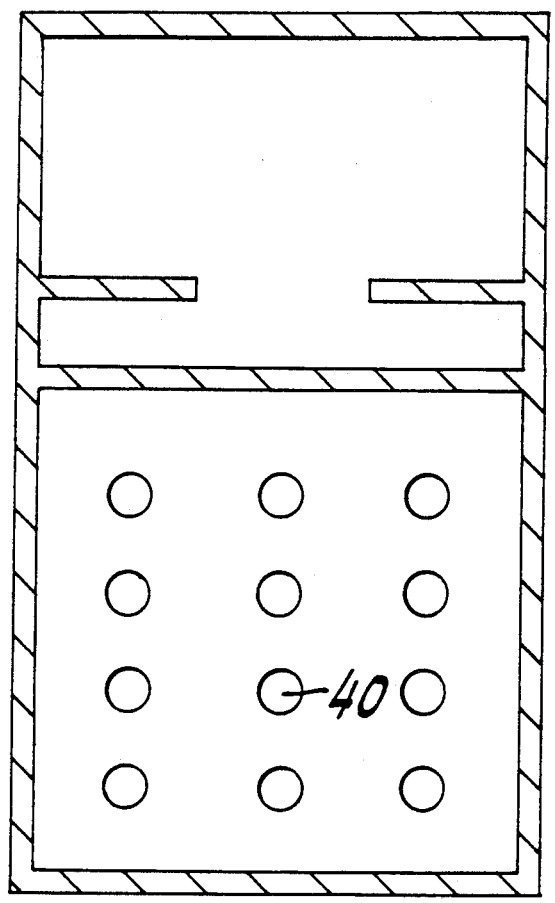
FIG. 5 is a schematic front elevational view of yet another alternate embodiment of the invention.

Yet another embodiment having a plurality of apertures 40 is shown in FIG. 5. An adhesive pad similar to that shown in FIG. 4 could also be used with this embodiment.

Figure 6:
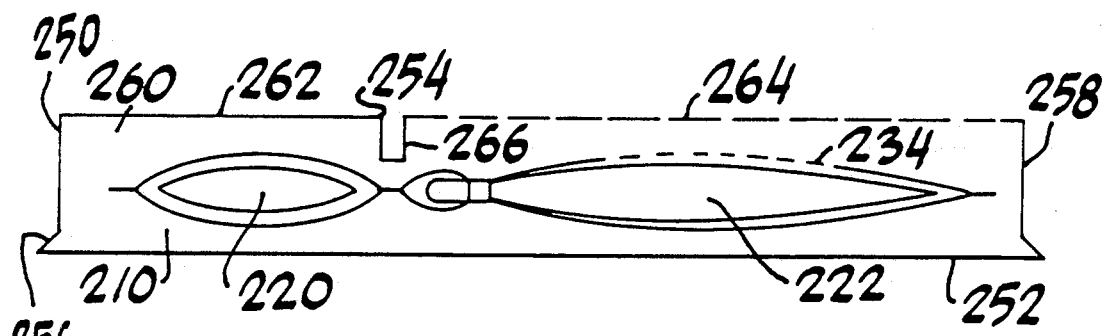
FIG. 6 is a diagrammatic side elevational cross-sectional view of one preferred embodiment of the invention enclosed within an outer shell.

Yet another embodiment of the invention is shown in FIG. 6. This embodiment is an air freshener and provides all of the advantages of the invention in a package which may be decorative and/or adapted to enable the invention to be used in a variety of environments. Multiple compartment, flexible package 210 is constructed similarly to packages discussed above and contains an inner rupturable capsule 220, an absorbent member 222 and an aperture 234. The entire package 210 is held within an outer shell 250, the shell being substantially impermeable to the liquid contents of inner pouch 220. Shell 250 comprises a planar back sheet 252, a thermal formed top sheet 254, the top and back sheets being secured along perimeter 256. Top sheet 254 has four downwardly depending side walls 258 thereby forming an enclosure 260 which contains package 210. The top surface of top portion 254 is somewhat firm but still pliable enough to enable the opposing sides of shell 250 to be squeezed together to rupture inner pouch 220. The top portion 254 may be divided into a planar, non-apertured face 262 and a planar apertured face 264, separated by a molded rib 266, if desired. Rib 266 adds to the structural integrity of the top portion 254. Package 210 may be loosely held within space 260 or may be secured, if desired. In either event, the advantage offered by shell 250 is that package 210 may be uniformly manufactured for use as a cleaning wipe or as an air freshener depending upon the liquid contents of inner pouch 220. Package 210 could be easily adapted for use as an air freshener merely by changing the liquid contents of the inner pouch 220 and by placing package 210 in an outer shell 250. When used as an air freshener, shell 250 could be either decorative and lie flat upon a surface or could be provided with adhesive means (not shown) to enable it to be secured in any orientation at a desired location.

The preferred embodiment has three main advantages over prior art devices: the force directing feature tending to reduce the force imposed upon the seal of the outer pouch, efficient mixing when two or more liquids are contained in separate inner storage pouches and the ability to provide apertures adjacent the surface of the absorbent pad without increasing the risk of leakage from the flexible package.

It will be understood by those skilled in the art that numerous other modifications and improvements may be made to the preferred embodiment of the invention disclosed herein without departing from the spirit and scope thereof.

What is claimed is:

1. A multiple compartment package comprising:
    a generally flat outer pouch comprising a pair of peripherally sealed, pliable sheet members, said outer pouch provided with at least one aperture in the surface of at least one of said sheet members;
    at least one inner pouch containing a liquid, said inner pouch situated within said outer pouch and adapted to rupture upon the application of pressure through said outer pouch to thereby release its contents into said outer pouch;
    an absorbent member interposed between said inner pouch and said aperture, said absorbent member having opposing surfaces sealingly secured transversely to both facing internal surfaces of said outer pouch intermediate said inner pouch and said aperture in a manner such that said absorbent member absorbs substantially all of the contents released from said inner pouch;
    said sheet members being partially transversely sealed together intermediate said inner pouch and said absorbent member and producing along the seal a passageway formed in the area between said sheet members, said passageway adapted to direct the flow of said liquid onto said absorbent member upon the rupture of said inner pouch.

2. A multiple compartment package according to claim 1 wherein said outer pouch is generally rectilinear and wherein only one surface of one of said pliable sheet members is provided with an aperture and further comprising:
    adhesive means secured to the non-apertured sheet member adjacent one end of said outer pouch, said adhesive means enabling said one end to be secured to the other end of said outer pouch.

3. A multiple compartment package comprising:
    a receiving compartment formed from a pair of peripherally sealed, pliable first sheet members;
    at least one liquid bearing inner container within said receiving compartment, said inner container adapted to be ruptured upon the application of pressure to release the contents of said inner container into said receiving compartment;
    a dispensing compartment for receiving the liquid contents of said inner container from said receiving compartment, said dispensing compartment formed from a pair of peripherally sealed, pliable second sheet members, at least a portion of the surface of at least one of the sheet members of said dispensing compartment provided with an area through which said liquid contents could be dispensed;
    an absorbent member within said dispensing compartment for absorbing said contents; and
    passageway means interposed between said receiving compartment and said dispensing compartment for directing said contents onto said absorbent member.

4. A multiple compartment package according to claim 3 wherein one of either said receiving or dispensing compartments has at least one side complementarily shaped to a side of the other, said receiving and dispensing compartments being joined along said complementarily shaped sides.

5. A multiple compartment package according to claim 3 wherein at least one of said second sheet members is provided with at least one aperture adjacent said absorbent member.

6. A multiple compartment package according to claim 5 wherein said contents are liquid which is vaporizable from the surface of said absorbent member exposed to ambient through said aperture.

7. A multiple compartment package according to claim 3 wherein at least one of said second sheet members is provided with a liquid permeable area through which said liquid contents may diffuse to the ambient.

8. A multiple compartment package according to claim 3 wherein each of said first sheet members is integrally formed with a respective one of said second sheet members.

* * * * *